(12) United States Patent
Forrest et al.

(10) Patent No.: US 10,634,048 B2
(45) Date of Patent: Apr. 28, 2020

(54) SYSTEM AND METHOD FOR POWER PRODUCTION INCLUDING METHANATION

(71) Applicant: 8 Rivers Capital, LLC, Durham, NC (US)

(72) Inventors: Brock Alan Forrest, Durham, NC (US); Xijia Lu, Durham, NC (US)

(73) Assignee: 8 RIVERS CAPITAL, LLC, Durham, NC (US)

( * ) Notice: Subject to any disclaimer, the term of this patent is extended or adjusted under 35 U.S.C. 154(b) by 503 days.

(21) Appl. No.: 15/434,218

(22) Filed: Feb. 16, 2017

(65) Prior Publication Data

US 2017/0241338 A1 Aug. 24, 2017

Related U.S. Application Data

(60) Provisional application No. 62/296,730, filed on Feb. 18, 2016.

(51) Int. Cl.
*F02C 3/22* (2006.01)
*C01B 3/38* (2006.01)
(Continued)

(52) U.S. Cl.
CPC .................. *F02C 3/22* (2013.01); *C01B 3/02* (2013.01); *C01B 3/386* (2013.01); *C07C 1/0435* (2013.01);
(Continued)

(58) Field of Classification Search
CPC ..... Y02E 20/16; Y02E 20/344; Y02E 20/322; Y02E 20/185; Y02E 20/328; F02C 3/34; C01B 2203/0261; C01B 2300/1846
See application file for complete search history.

(56) References Cited

U.S. PATENT DOCUMENTS

| 3,369,361 A | 2/1968 | Craig |
| 3,376,706 A | 4/1968 | Angelino |

(Continued)

FOREIGN PATENT DOCUMENTS

| JP | 2225905 | 9/1990 |
| JP | 2001-132472 | 5/2001 |
| WO | WO 95/12757 | 5/1995 |

OTHER PUBLICATIONS

Combs, Jr. "An Investigation of the Supercritical CO2 Cycle (Feher Cycle) for Shipboard Application," 1977, *Submitted in Partial Fulfillment of the Requirements for the Degree of Ocean Engineer and the Degree of Master of Science in Mechanical Engineering at the Massachusetts Institute of Technology*, 148.

(Continued)

*Primary Examiner* — Imran Akram
(74) *Attorney, Agent, or Firm* — Womble Bond Dickinson (US) LLP (57) ABSTRACT

The present disclosure relates to a power production system that is adapted to achieve high efficiency power production with carbon capture when using a solid or liquid hydrocarbon or carbonaceous fuel. More particularly, the solid or liquid fuel first is partially oxidized in a partial oxidation reactor that is configured to provide an output stream that is enriched in methane content. The resulting partially oxidized stream can be cooled, filtered, additionally cooled, and then directed to a combustor of a power production system as the combustion fuel. The partially oxidized stream is combined with a compressed recycle $CO_2$ stream and oxygen. The combustion stream is expanded across a turbine to produce power and passed through a recuperator heat exchanger. The recycle $CO_2$ stream is compressed and passed through the recuperator heat exchanger and option- (Continued)

ally the POX heat exchanger in a manner useful to provide increased efficiency to the combined systems.

20 Claims, 2 Drawing Sheets

(51) Int. Cl.
| | |
|---|---|
| *F02C 3/28* | (2006.01) |
| *C10J 3/82* | (2006.01) |
| *C07C 1/04* | (2006.01) |
| *C01B 3/02* | (2006.01) |
| *C10J 3/02* | (2006.01) |
| *C10J 3/00* | (2006.01) |
| *C10K 1/20* | (2006.01) |
| *C10K 1/00* | (2006.01) |
| *C10K 1/02* | (2006.01) |
| *C10J 3/46* | (2006.01) |
| *C10K 3/04* | (2006.01) |

(52) U.S. Cl.
CPC . *C10J 3/00* (2013.01); *C10J 3/02* (2013.01); *C10J 3/466* (2013.01); *C10J 3/82* (2013.01); *C10K 1/004* (2013.01); *C10K 1/005* (2013.01); *C10K 1/007* (2013.01); *C10K 1/024* (2013.01); *C10K 1/20* (2013.01); *C10K 3/04* (2013.01); *F02C 3/28* (2013.01); *C01B 2203/0261* (2013.01); *C01B 2203/062* (2013.01); *C01B 2203/1235* (2013.01); *C07C 2523/755* (2013.01); *C10J 2300/093* (2013.01); *C10J 2300/0959* (2013.01); *C10J 2300/0976* (2013.01); *C10J 2300/0986* (2013.01); *C10J 2300/165* (2013.01); *C10J 2300/1606* (2013.01); *C10J 2300/1621* (2013.01); *C10J 2300/1643* (2013.01); *C10J 2300/1653* (2013.01); *C10J 2300/1662* (2013.01); *C10J 2300/1675* (2013.01); *C10J 2300/1815* (2013.01); *C10J 2300/1846* (2013.01); *C10J 2300/1876* (2013.01); *C10J 2300/1884* (2013.01); *C10J 2300/1892* (2013.01); *Y02E 20/344* (2013.01)

(56) References Cited

U.S. PATENT DOCUMENTS

| | | | |
|---|---|---|---|
| 3,503,208 A | | 3/1970 | Schmidt |
| 3,544,291 A | | 12/1970 | Schlinger et al. |
| 3,723,345 A | * | 3/1973 | Reynolds ............... C01B 32/40 252/373 |
| 3,736,745 A | | 6/1973 | Karig |
| 3,740,204 A | * | 6/1973 | Slater et al. ............ C07C 1/02 48/215 |
| 3,837,788 A | | 9/1974 | Craig et al. |
| 3,868,817 A | | 3/1975 | Marion et al. |
| 3,888,043 A | * | 6/1975 | Child .................... C07C 1/0485 48/197 R |
| 3,938,968 A | * | 2/1976 | White .................... C01B 3/22 48/215 |
| 3,954,424 A | * | 5/1976 | Goeke ................... B01D 53/34 48/215 |
| 3,958,956 A | * | 5/1976 | Goeke ................... C01B 3/22 48/62 R |
| 3,971,211 A | | 7/1976 | Wethe et al. |
| 3,976,443 A | | 8/1976 | Paull et al. |
| 4,121,912 A | | 10/1978 | Barber et al. |
| 4,132,065 A | | 1/1979 | McGann |
| 4,154,581 A | | 5/1979 | Nack et al. |
| 4,191,500 A | | 3/1980 | Oberg et al. |
| 4,193,259 A | | 3/1980 | Muenger et al. |
| 4,206,610 A | | 6/1980 | Santhanam |
| 4,461,154 A | | 7/1984 | Allam |
| 4,483,691 A | * | 11/1984 | McShea, III ........... C01B 3/382 252/373 |
| 4,498,289 A | | 2/1985 | Osgerby |
| 4,522,628 A | | 6/1985 | Savins |
| 4,602,483 A | | 7/1986 | Wilks et al. |
| 4,702,747 A | | 10/1987 | Meyer et al. |
| 4,721,420 A | | 1/1988 | Santhanam et al. |
| 4,765,143 A | | 8/1988 | Crawford et al. |
| 4,765,781 A | | 8/1988 | Wilks et al. |
| 4,839,030 A | | 6/1989 | Comolli et al. |
| 4,852,996 A | | 8/1989 | Knop et al. |
| 4,881,366 A | | 11/1989 | Nurse |
| 4,957,515 A | | 9/1990 | Hegarty |
| 4,999,992 A | | 3/1991 | Nurse |
| 4,999,995 A | | 3/1991 | Nurse |
| 5,175,995 A | | 1/1993 | Pak et al. |
| 5,247,791 A | | 9/1993 | Pak et al. |
| 5,265,410 A | | 11/1993 | Hisatome |
| 5,319,924 A | | 6/1994 | Wallace et al. |
| 5,345,756 A | | 9/1994 | Jahnke et al. |
| 5,353,721 A | | 10/1994 | Mansour et al. |
| 5,394,686 A | | 3/1995 | Child et al. |
| 5,415,673 A | | 5/1995 | Hilton et al. |
| 5,421,166 A | | 6/1995 | Allam et al. |
| 5,507,141 A | | 4/1996 | Stigsson |
| 5,520,894 A | | 5/1996 | Heesink et al. |
| 5,590,519 A | | 1/1997 | Almlöf et al. |
| 5,595,059 A | | 1/1997 | Huber et al. |
| 5,641,327 A | * | 6/1997 | Leas ..................... C10J 3/00 48/197 R |
| 5,692,890 A | | 12/1997 | Graville |
| 5,709,077 A | | 1/1998 | Beichel |
| 5,715,673 A | | 2/1998 | Beichel |
| 5,724,805 A | | 3/1998 | Golomb et al. |
| 5,802,840 A | | 9/1998 | Wolf |
| 5,906,806 A | | 5/1999 | Clark |
| 5,937,652 A | | 8/1999 | Abdelmalek |
| 6,024,029 A | | 2/2000 | Clark |
| 6,117,916 A | | 9/2000 | Allam et al. |
| 6,148,602 A | | 11/2000 | Demetri |
| 6,170,264 B1 | | 1/2001 | Viteri et al. |
| 6,196,000 B1 | | 3/2001 | Fassbender |
| 6,199,364 B1 | | 3/2001 | Kendall et al. |
| 6,202,574 B1 | | 3/2001 | Liljedahl et al. |
| 6,209,307 B1 | | 4/2001 | Hartman |
| 6,260,348 B1 | | 7/2001 | Sugishita et al. |
| 6,263,661 B1 | | 7/2001 | Van der Burgt et al. |
| 6,269,624 B1 | | 8/2001 | Frutschi et al. |
| 6,289,666 B1 | | 9/2001 | Ginter |
| 6,298,664 B1 | | 10/2001 | Åsen et al. |
| 6,306,917 B1 | | 10/2001 | Bohn et al. |
| 6,333,015 B1 | | 12/2001 | Lewis |
| 6,360,561 B2 | | 3/2002 | Allam et al. |
| 6,389,814 B2 | | 5/2002 | Viteri et al. |
| 6,430,916 B2 | | 8/2002 | Sugishita et al. |
| 6,532,745 B1 | | 3/2003 | Neary |
| 6,536,205 B2 | | 3/2003 | Sugishita et al. |
| 6,543,214 B2 | | 4/2003 | Sasaki et al. |
| 6,550,234 B2 | | 4/2003 | Guillard |
| 6,598,398 B2 | | 7/2003 | Viteri et al. |
| 6,612,113 B2 | | 9/2003 | Guillard |
| 6,622,470 B2 | | 9/2003 | Viteri et al. |
| 6,629,414 B2 | | 10/2003 | Fischer |
| 6,637,183 B2 | | 10/2003 | Viteri et al. |
| 6,684,643 B2 | | 2/2004 | Frutschi |
| 6,764,530 B2 | | 7/2004 | Lijima |
| 6,775,987 B2 | | 8/2004 | Sprouse et al. |
| 6,802,178 B2 | | 10/2004 | Sprouse et al. |
| 6,820,689 B2 | | 11/2004 | Sarada |
| 6,824,710 B2 | | 11/2004 | Viteri et al. |
| 6,871,502 B2 | | 3/2005 | Marin et al. |
| 6,877,319 B2 | | 4/2005 | Linder et al. |
| 6,877,322 B2 | | 4/2005 | Fan |
| 6,898,936 B1 | | 5/2005 | Ochs et al. |
| 6,910,335 B2 | | 6/2005 | Viteri et al. |
| 6,912,004 B1 | | 6/2005 | Knudsen et al. |
| 6,918,253 B2 | | 7/2005 | Fassbender |
| 6,945,029 B2 | | 9/2005 | Viteri |

(56) References Cited

U.S. PATENT DOCUMENTS

| | | |
|---|---|---|
| 6,945,052 B2 | 9/2005 | Frutschi et al. |
| 6,993,912 B2 | 2/2006 | Fischer |
| 7,007,474 B1 | 3/2006 | Ochs et al. |
| 7,007,486 B2 | 3/2006 | Sprouse et al. |
| 7,021,063 B2 | 4/2006 | Viteri |
| 7,022,168 B2 | 4/2006 | Schimkat et al. |
| 7,043,920 B2 | 5/2006 | Viteri et al. |
| 7,074,033 B2 | 7/2006 | Neary |
| 7,089,743 B2 | 8/2006 | Frutschi et al. |
| 7,111,463 B2 | 9/2006 | Sprouse et al. |
| 7,124,589 B2 | 10/2006 | Neary |
| 7,147,461 B2 | 12/2006 | Neary |
| 7,191,587 B2 | 3/2007 | Marin et al. |
| 7,192,569 B2 | 3/2007 | Stewart |
| 7,281,590 B2 | 10/2007 | Van de Waal |
| 7,284,362 B2 | 10/2007 | Marin et al. |
| 7,299,637 B2 | 11/2007 | Becker |
| 7,303,597 B2 | 12/2007 | Sprouse et al. |
| 7,328,581 B2 | 2/2008 | Christensen et al. |
| 7,334,631 B2 | 2/2008 | Kato et al. |
| 7,360,639 B2 | 4/2008 | Sprouse et al. |
| 7,363,764 B2 | 4/2008 | Griffin et al. |
| 7,377,111 B2 | 5/2008 | Agnew |
| 7,387,197 B2 | 6/2008 | Sprouse et al. |
| 7,402,188 B2 | 7/2008 | Sprouse |
| 7,469,544 B2 | 12/2008 | Farhangi |
| 7,469,781 B2 | 12/2008 | Chataing et al. |
| 7,516,607 B2 | 4/2009 | Farhangi et al. |
| 7,516,609 B2 | 4/2009 | Agnew |
| 7,547,419 B2 | 6/2009 | Sprouse et al. |
| 7,547,423 B2 | 6/2009 | Sprouse et al. |
| 7,553,463 B2 | 6/2009 | Zauderer |
| 7,615,198 B2 | 11/2009 | Sprouse et al. |
| 7,665,291 B2 | 2/2010 | Anand et al. |
| 7,717,046 B2 | 5/2010 | Sprouse et al. |
| 7,722,690 B2 | 5/2010 | Shires et al. |
| 7,731,783 B2 | 6/2010 | Sprouse et al. |
| 7,739,874 B2 | 6/2010 | Nigro |
| 7,740,671 B2 | 6/2010 | Yows et al. |
| 7,740,672 B2 | 6/2010 | Sprouse |
| 7,814,975 B2 | 10/2010 | Hagen et al. |
| 7,826,054 B2 | 11/2010 | Zillmer et al. |
| 7,827,794 B1 | 11/2010 | Pronske et al. |
| 7,874,140 B2 | 1/2011 | Fan et al. |
| 7,882,692 B2 | 2/2011 | Pronske et al. |
| 7,927,574 B2 | 4/2011 | Stewart |
| 7,934,383 B2 | 5/2011 | Gutierrez et al. |
| 7,950,243 B2 | 5/2011 | Gurin |
| 8,043,588 B2 | 10/2011 | Hustad et al. |
| 8,088,196 B2 | 1/2012 | White et al. |
| 8,109,095 B2 | 2/2012 | Henriksen et al. |
| 8,220,248 B2 | 7/2012 | Wijmans et al. |
| 2002/0103264 A1 | 8/2002 | Allam et al. |
| 2002/0121092 A1 | 9/2002 | Allam et al. |
| 2002/0134085 A1 | 9/2002 | Frutschi |
| 2003/0119919 A1 | 6/2003 | Allam et al. |
| 2003/0131582 A1 | 7/2003 | Anderson et al. |
| 2004/0011057 A1 | 1/2004 | Huber |
| 2004/0123601 A1 | 7/2004 | Fan |
| 2004/0134197 A1 | 7/2004 | Marin et al. |
| 2005/0126156 A1 | 6/2005 | Anderson et al. |
| 2006/0242907 A1 | 11/2006 | Sprouse et al. |
| 2007/0122328 A1 | 5/2007 | Allam et al. |
| 2007/0130957 A1 | 6/2007 | Hoffmann et al. |
| 2007/0180768 A1 | 8/2007 | Briesch et al. |
| 2007/0186474 A1* | 8/2007 | Rabovitser ............ B01J 19/088 48/197 R |
| 2007/0274876 A1 | 11/2007 | Chiu et al. |
| 2008/0010967 A1 | 1/2008 | Griffin et al. |
| 2008/0104958 A1 | 5/2008 | Finkenrath et al. |
| 2008/0115500 A1 | 5/2008 | MacAdam et al. |
| 2008/0166672 A1 | 7/2008 | Schlote et al. |
| 2008/0173584 A1 | 7/2008 | White et al. |
| 2008/0173585 A1 | 7/2008 | White et al. |
| 2008/0176174 A1 | 7/2008 | White et al. |
| 2008/0187877 A1 | 8/2008 | Fitzsimmons et al. |
| 2008/0190214 A1 | 8/2008 | Ubowski et al. |
| 2008/0226515 A1 | 9/2008 | Allam et al. |
| 2008/0309087 A1 | 12/2008 | Evulet et al. |
| 2009/0025390 A1 | 1/2009 | Christensen et al. |
| 2009/0061264 A1 | 3/2009 | Agnew |
| 2009/0130660 A1 | 5/2009 | Faham et al. |
| 2009/0229271 A1 | 9/2009 | De Ruyck et al. |
| 2009/0260585 A1 | 10/2009 | Hack et al. |
| 2009/0301054 A1 | 12/2009 | Simpson et al. |
| 2009/0324462 A1* | 12/2009 | Robinson ................ C10J 3/00 422/187 |
| 2010/0018218 A1 | 1/2010 | Riley et al. |
| 2010/0024378 A1 | 2/2010 | Ackermann et al. |
| 2010/0024381 A1 | 2/2010 | Ackermann et al. |
| 2010/0024433 A1 | 2/2010 | Ackermann et al. |
| 2010/0031668 A1 | 2/2010 | Kepplinger |
| 2010/0077752 A1 | 4/2010 | Papile |
| 2010/0086451 A1 | 4/2010 | Allam |
| 2010/0121125 A1* | 5/2010 | Hippo ..................... B01J 21/18 585/733 |
| 2010/0175320 A1 | 7/2010 | Schuetzle et al. |
| 2010/0263385 A1 | 10/2010 | Allam |
| 2010/0324156 A1 | 12/2010 | Winter et al. |
| 2011/0023539 A1 | 2/2011 | White et al. |
| 2011/0036011 A1 | 2/2011 | Sprouse et al. |
| 2011/0062721 A1 | 3/2011 | Sirdeshpande et al. |
| 2011/0127773 A1 | 6/2011 | Freund et al. |
| 2011/0179799 A1 | 7/2011 | Allam et al. |
| 2011/0233940 A1 | 9/2011 | Aoyama et al. |
| 2011/0239651 A1 | 10/2011 | Aoyama et al. |
| 2011/0271713 A1 | 11/2011 | White et al. |
| 2012/0131925 A1 | 5/2012 | Mittricker et al. |
| 2012/0247105 A1 | 10/2012 | Nelson et al. |
| 2012/0308172 A1 | 12/2012 | Shaikh |
| 2013/0118891 A1 | 5/2013 | Allam |
| 2013/0205746 A1 | 8/2013 | Allam et al. |
| 2014/0170029 A1 | 6/2014 | Allam |

OTHER PUBLICATIONS

Dostal et al., "A Supercritical Carbon Dioxide Cycle for Next Generation Nuclear Reactors," 2004, (*Research Paper*) *Advanced Nuclear Power Technology Program at MIT*, 326 pages.

Hong et al., "Analysis of Oxy-Fuel Combustion Power Cycle Utilizing a Pressurized Coal Combustor," *Energy*, Available Online Jun. 21, 2009, pp. 1332-1340, vol. 34, No. 9.

Iantovski et al., "Highly Efficient Zero Emission CO2-Based Power Plant" *Energy Convers. Mgmt*, 1997, Suppl. pp. S141-S146, vol. 38.

E.I. Yantovskii et al., "Computer Exergonomics of Power Plants Without Exhaust Gases," Energy Convers. Mgmt., Publ. 1992, vol. 33, No. 5-8, pp. 405-412.

Mathieu et al., "Sensitivity Analysis of the MATIANT Cycle", *Energy Conversion & Management*, 1999, pp. 1687-1700, vol. 40.

Wall et al., "A Zero Emission Combustion Power Plant for Enhanced Oil Recovery," *Energy*, 1995, pp. 823-828, vol. 20, No. 8.

http://www.graz-cycle.tugraz.at/pdfs/Bolland_Kvamsdal_Boden_Liege.pdf; Boland, "A Thermodynamic Comparison of the Oxy-Fuel Power Cycles Water-Cycle, Graz-Cycle and Matiant-Cycle," *Norwegian University of Science and Technology*, Trondheim, Norway. Presentation, paper published in the proceedings of the International Conference Power Generation and Sustainable Development, Liège (Belgium), Oct. 8-9, 2001.

http://www2.ulg.ac.be/genienuc/pageco2.htm; Université de Liège, Department of Power Generation, "CO2 Researches" Web-page dated Sep. 1, 1998 (retrieved on Feb. 25, 2011).

\* cited by examiner

SYSTEM AND METHOD FOR POWER PRODUCTION INCLUDING METHANATION

FIELD OF THE DISCLOSURE

The present invention is directed to systems and methods for generation of power, such as electricity. Particularly, the systems and methods can provide a fuel material with an increased methane content following partial oxidation of a fuel.

BACKGROUND

Conventional means of power production from combustion of a fuel typically lack the ability to simultaneously achieve both high efficiency power generation and carbon capture. This limitation is magnified when using solid fuels in the combustion reaction because of the solid and inert nitrogen gas contents remaining in the combustion product stream. Accordingly, there is an ever growing need in the art for systems and methods for high efficiency power generation allowing for a reduction in $CO_2$ emission and/or improved ease of sequestration of produced carbon dioxide.

One publication in the field of high efficiency power generation with carbon capture, U.S. Pat. No. 8,596,075 to Allam et al., provides one solution whereby a solid fuel such as coal, lignite, pet-coke or biomass is gasified by reaction with oxygen and optionally steam in a partial oxidation reactor operating at a sufficiently high pressure and temperature to allow substantially complete conversion of the solid fuel to a gaseous fuel comprising mainly carbon monoxide and hydrogen as the combustible components together with combustion derived impurities, such as $H_2S$, $CS_2$, carbonyl sulfide (COS), HCN, and $NH_3$. The partially oxidized net product gas is cooled, ash is separated, and it is optionally compressed to allow it to be introduced as fuel into the combustion chamber of the power generation system. The operating pressure of the partial oxidation system and the power generation system can be such that no compression of the fuel gas is required. The power generation system combustor operates with an excess of $O_2$ present following combustion, which ensures that the fuel and combustion derived impurities are converted from the reduced state to their oxidized forms comprising predominantly $SO_2$ and NO. The partial oxidation reactor can be provided with transpirationally cooled walls with a high pressure recycle $CO_2$ stream cooling the partial oxidation product gas before ash removal at a temperature level of about 800° C. Further cooling of the partial oxidation gas to about 400° C. is necessary to ensure that all fine ash particles together with solidified volatile inorganic components are condensed and filtered to prevent solid deposition, corrosion, and blockage of down-stream equipment. The cooling of the partial oxidation gas from 800° C. to 400° C. must take place in a heat exchanger with tubes for the high pressure partial oxidation gas that are resistant to metal dusting corrosion due to the Boudouard carbon forming reaction and the high CO partial pressure in the partial oxidation gas. This is shown below in Formula (1).

$$CO+CO=C+CO_2 \tag{1}$$

The tubes must be designed to allow periodic water washing to remove solid deposits derived from the condensation of volatile inorganic components present in solid fuels, particularly coal and lignite.

Despite the advances of the above-described publication, the systems and methods described therein still do not provide a most advantageous solution to the problems arising when using solid fuels as a power production combustion fuel. Thus, there remains a need for further systems and methods for high efficiency combustion of solid fuels with carbon capture.

BRIEF SUMMARY OF THE DISCLOSURE

The present disclosure provides systems and methods for power production wherein a solid or liquid fuel can be partially oxidized, and the partially oxidized stream can be passed to a power production system. In particular, the systems and methods can be configured so that the partially oxidized stream is enriched in methane content.

In one or more embodiments, the present disclosure can provide a process for the production of power using a combination of a partial oxidation (POX) system and a power production system (PPS), the process comprising:

combining a solid or liquid fuel, oxygen, and a catalyst in a POX reactor under conditions sufficient to partially oxidize the fuel and form a POX stream comprising a fuel gas including methane;

cooling the POX stream to a temperature of about 500° C. or less;

separating one or more of solids, molten metals, and acid gases from the POX stream;

passing the POX stream to a POX heat exchanger and withdrawing a quantity of heat from the POX stream by cooling the POX stream to a temperature of about 100° C. or less against a cooling stream and form a POX fuel gas stream;

passing the POX fuel gas stream through a separator vessel and separating at least a portion of any water present in the POX fuel gas stream;

compressing the POX fuel gas stream to a pressure of about 12 MPa or greater;

combusting the POX fuel gas in a PPS combustor to form a combustion product stream at a pressure of at least about 10 MPa and a temperature of at least about 800° C.; and expanding the combustion product stream across a PPS turbine to generate power and form an expanded PPS combustion product stream;

wherein the POX fuel gas stream that is pressurized has a methane content of about 20% or greater by volume, preferably a methane content of about 30% or greater, about 50% or greater, about 60% or greater, about 70% or greater, about 80% or greater, about 90% or greater, or about 95% or greater by volume based on the total volume of the POX fuel gas stream.

In further embodiments the power production process can be defined in relation to one or more of the following statements, which can be combined in any number and order.

The catalyst can be selected from the group consisting of alkali metals, alkaline earth metals, transition metals, compounds thereof, complexes thereof, and combinations thereof.

The POX reactor can be operated at a temperature of about 1000° C. or less, preferably about 800° C. or less, or about 600° C. or less.

The process can further comprise adding steam to the POX reactor.

The cooling of the POX stream from the POX reactor can comprise passing the POX stream through a convective cooler against a cooling stream, which cooling stream can preferably comprise one or more of: a high pressure recycle fluid stream withdrawn from and returned to the PPS; a high pressure water stream; a nitrogen stream; a high pressure stream of $O_2$ and $CO_2$; a stream of POX reactor liquid fuel feed; and a stream of cleaned and cooled POX fuel gas.

The solids separated from the POX stream can comprise one or more of ash particles, unreacted char, and catalyst.

The separating of the one more of solids, molten metals, and acid gases from the POX stream can comprise passing the POX stream through a particle filter and a water scrubber.

Prior to the step of passing the POX stream to the POX heat exchanger, the process can include passing at least a portion of the POX stream through a catalytic water gas shift reactor configured to convert CO and $H_2O$ in the POX stream to $CO_2$ and $H_2$.

The POX fuel gas exiting the catalytic water gas shift reactor can have an $H_2$ to CO ratio of about 5:1 to about 1:1.

Prior to the step of passing the POX stream to the POX heat exchanger, the process can include passing at least a portion of the POX stream through a carbonyl sulfide (COS) hydrolysis reactor configured to convert COS to $H_2S$.

The POX stream passed through the POX heat exchanger can be cooled against a cooling stream comprising one or more of: a high pressure recycle fluid stream withdrawn from and returned to the PPS; a high pressure water stream; a nitrogen stream; a high pressure stream of $O_2$ and $CO_2$; a stream of POX reactor liquid fuel feed; and a stream of cleaned and cooled POX fuel gas.

Prior to the step of compressing the POX fuel gas stream to a pressure of about 12 MPa or greater, at least a portion of the POX fuel gas stream can be passed through one or both of a mercury removal unit and an acid gas removal unit.

At least a portion of the POX fuel gas stream can be passed through an activated, sulfur-impregnated, carbon bed adsorption system configured to remove mercury from the POX fuel gas.

At least a portion of the POX fuel gas stream can be passed through an acid gas removal unit configured to remove part or substantially all of at least one of $H_2S$ and $CO_2$ from the POX fuel gas stream.

Prior to the step of compressing the POX fuel gas stream to a pressure of about 12 MPa or greater, at least a portion of the POX fuel gas stream can be passed through a methanation unit configured to convert CO and $H_2$ to $CH_4$ and $H_2O$.

The methanation unit can be a catalytic unit, and the methanation optionally can be carried out using a nickel-based catalyst.

The POX fuel gas exiting the methanation unit can have a methane content of about 75% or greater by volume.

The methanation unit can produce heat from an exothermic methanation reaction, and such produced heat can be absorbed by passing the POX fuel gas exiting the methanation unit through a post-methanation heat exchanger against a cooling stream, which cooling stream can preferably comprise one or more of: a high pressure recycle fluid stream withdrawn from and returned to the PPS; a high pressure water stream; a nitrogen stream; a high pressure stream of $O_2$ and $CO_2$; a stream of POX reactor liquid fuel feed; and a stream of cleaned and cooled POX fuel gas.

The process can comprise passing the POX fuel gas stream from the methanation unit to a separator wherein at least a portion of any water produced in the methanation reactor is removed.

After said step of compressing the POX fuel gas stream to a pressure of about 12 MPa or greater and prior to said step of combusting the POX fuel gas in the PPS combustor, the process can comprise heating the compressed POX fuel gas by passage through the POX heat exchanger;

The process further can comprise: passing the expanded PPS combustion product stream through a PPS recuperator heat exchanger and thereby withdrawing heat from the PPS combustion product stream and forming a cooled PPS combustion product stream; optionally passing the cooled PPS combustion product stream through a water cooler; treating the cooled PPS combustion product stream in a PPS scrubber to form a recycle $CO_2$ stream by removing substantially all non$CO_2$ components; and pressurizing the recycle $CO_2$ stream in a PPS compressor to form a compressed recycle $CO_2$ stream.

In one or more embodiments, the present disclosure can specifically provide a combined partial oxidation (POX) system and power production system (PPS). For example, such system can comprise:

a catalytic POX reactor adapted to partially oxidize a liquid or solid fuel in the presence of oxygen, a catalyst, and optionally steam to form a POX stream comprising a fuel gas;

one or more components adapted to cool the POX stream;

a POX heat exchanger adapted to withdraw heat from the POX stream and output a cooled POX fuel gas;

an optional mercury removal unit;

an optional acid gas removal unit;

an optional methanation unit;

an optional post-methanation heat exchanger configured to withdraw heat from a stream exiting a methanation unit;

a compressor adapted to compress the POX fuel gas to a pressure of about 10 MPa or greater;

a PPS combustor adapted to combust the POX fuel gas in the presence of oxygen and a compressed recycle $CO_2$ stream and form a PPS combustion product stream at a pressure of about 10 MPa or greater;

a turbine adapted to expand the PPS combustion product stream and generate power in a connected generator;

a recuperator heat exchanger adapted to withdraw heat from the expanded PPS combustion product stream and add the heat to the compressed recycle $CO_2$ stream;

a PPS compressor adapted to compress the recycle $CO_2$ stream to a pressure of about 10 MPa or greater and form the compressed recycle $CO_2$ stream;

optional flow components adapted to direct a portion of the compressed recycle $CO_2$ stream to the POX heat exchanger;

optional flow components adapted to direct a portion of the compressed recycle $CO_2$ stream to the PPS recuperator heat exchanger; and optional flow components adapted to direct the compressed recycle $CO_2$ stream from the POX heat exchanger to the PPS recuperator heat exchanger.

BRIEF DESCRIPTION OF THE DRAWINGS

Having thus described the invention in general terms, reference will now be made to the accompanying drawings, which is not necessarily drawn to scale, and wherein:

DETAILED DESCRIPTION OF THE DISCLOSURE

The invention now will be described more fully hereinafter through reference to various embodiments. These embodiments are provided so that this disclosure will be thorough and complete, and will fully convey the scope of the invention to those skilled in the art. Indeed, the invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

The systems and methods of the present disclosure are adapted for achieving partial oxidation (POX) of a carbonaceous fuel, particularly a solid fuel and/or a liquid fuel. Non-limiting examples of fuels that can be used according to the present disclosure include coal, lignite, petroleum coke, bitumen, biomass, algae, wood, graded combustible solid waste refuse, asphalt, used tires, crude oil, other ash containing liquid fuels, and the like.

Partial oxidation of the carbonaceous fuel in the POX reactor forms a POX stream, which can be defined in terms of the components thereof. In particular, the POX stream can comprise a fuel gas and optionally one or more impurities (oxidizable impurities and non-oxidizable impurities). The POX fuel gas stream (including at least a portion of the impurities or being substantially free of any of the impurities, particularly the non-oxidizable impurities) can be input to a combustor in a power production system. For example, a combustor and associated power production cycle that can be combined with the systems and methods of the present disclosure is described in U.S. Pat. No. 8,596,075 to Allam et al., the disclosure of which is incorporated herein by reference. The process of the '075 patent achieves power generation using predominantly $CO_2$ as a working fluid. In particular, the process uses a turbine that expands a mixture of a high pressure recycle $CO_2$ stream and combustion products arising from combustion of the fuel. Pure oxygen can be used as the oxidant in the combustion process, and the oxidant may be diluted with recycled $CO_2$ prior to passing to the combustor. The hot turbine exhaust is used to partially preheat the high pressure recycle $CO_2$ stream. The recycle $CO_2$ stream is also heated using added heat that is not derived from the hot turbine exhaust. For example, compression energy of the air feed of an $O_2$ production plant may be used. All fuel and combustion derived impurities such as sulfur compounds, NO, $NO_2$, $CO_2$, $H_2O$, Hg and the like are separated for disposal with no emissions to the atmosphere.

The systems and methods of the present disclosure specifically can be characterized as being a combination of a POX system and power production system (PPS). The power cycle described in the '075 patent is an example of a PPS that can be used according to the present disclosure. In particular, a POX fuel gas stream can be introduced to the PPS combustor as part or all of the fuel stream for the combustor. In a high pressure combustion cycle, the fuel gas from the POX stream must in general be compressed to the high pressure required in the power production system combustor. For example, the POX fuel gas stream may be compressed in a compressor to a pressure of about 10 MPa or greater, about 15 MPa or greater, about 20 MPa or greater, or about 25 MPa or greater. In other embodiments, the pressure can be about 8 MPa to about 50 MPa, about 15 MPa to about 45 MPa, or about 20 MPa to about 40 MPa.

The combination of a POX system and a PPS system is described in U.S. Pat. No. 8,776,532 to Allam et al., the disclosure of which is incorporated herein by reference. The systems and methods of the present disclosure can incorporate a variety of aspects of the systems and methods described therein.

The POX fuel gas stream arising from the reaction of the oxygen with a solid or liquid fuel can comprise varying amounts of solids and molten solids that can be removed before introduction of the POX fuel gas stream into the PPS combustor. Specifically, the POX fuel gas stream can be cooled as necessary to a temperature wherein ash and other solid materials can be removed. This is beneficial to prevent downstream contamination of equipment in the POX system and the PPS. The heat liberated during cooling of the POX fuel gas stream can be transferred to the power production system to maximize overall efficiency of the power production system. In particular, this heat can be used for partially heating at least a portion of the recycle $CO_2$ fluid circulating in the power production after cooling of the combustion product stream and prior to input of the recycle $CO_2$ fluid back into the combustor of the power production system. In particular, the heat can be added to the recycle $CO_2$ fluid following the compression of the recycle $CO_2$ fluid. As a further example, this heat can be used for heating a fuel or a component of a fuel feed stream prior to passage to the POX reactor in order to reduce oxygen consumption in the POX reactor. Optionally a fuel stream and/or the oxygen passed to the POX reactor and/or passed to the power production system combustor can also be heated against the cooling POX stream in the same or a different heat exchanger.

The POX reactor can be adapted to provide an output POX fuel gas stream having a temperature that is about 600° C. or greater, about 800° C. or greater, about 1000° C. or greater, or about 1200° C. or greater. More particularly, the temperature can be about 600° C. to about 2000° C., about 700° C. to about 1800° C., or about 800° C. to about 1600° C. In various embodiments, one or more steps can be utilized to cool the POX stream (and thus the fuel gas for input to a further combustor), such as to about ambient temperature.

In one or more embodiments, the POX stream immediately exiting the POX reactor at a temperature as described above can be quenched to a lesser temperature. Alternatively or additionally, the POX stream can be passed through one or more coolers. Preferably, quenching and/or cooling reduces the temperature of the POX stream to about 500° C. or less, about 400° C. or less, or about 300° C. or less.

Quenching can be carried out by mixing of the POX stream with one or more quenching fluids. Non-limiting examples of quenching fluids that can be used according to the present disclosure include a stream of recycled POX product (i.e., at least a portion of the POX product that has been already cooled to a quenching fluid temperature then cooled in the POX gas heat exchanger followed by liquid water separation), water at a quenching fluid temperature, liquid $CO_2$, mixtures thereof, and the like. A useful quenching fluid temperature can be about 150° C. or less, about 100° C. or less, about 75° C. or less, or about 60° C. or less. The quenching fluid temperature particularly can be about 10° C. to about 150° C., about 15° C. to about 100° C., or about 20° C. to about 75° C. In embodiments using a water quench, a portion of the water can be vaporized thus giving a mixture of fuel gas, steam, and a liquid water portion, which washes out the bulk of the ash particles. The temperature of the total liquid and vapor will be determined by the pressure used in the POX reactor and the quantity of liquid water used for the quench.

In one or more embodiments, the present system and method can be configured for separation of any liquid water and the bulk of any ash particles or further solids from the cooled POX stream vapor. Removal of the solids can be carried out using any conventional separation or filter means. Non-limiting examples of suitable solids removal components include cyclone filters, settling tanks, candle filters, bag filters, liquid wash towers, and the like. Such components may be configured for removal of solids and/or soluble gases. For example, a water scrubber can be utilized.

The cooled POX stream can be further cooled, such as to near ambient temperature, using one or more heat exchangers. In particular, a heat exchanger can be adapted to transfer the heat from the quenched/cooled POX stream to one or more portions of the high pressure $CO_2$ recycle stream utilized in the power production system. For example, the heat can be transferred to the high pressure $CO_2$ recycle stream taken from the $CO_2$ recycle compressor discharge and/or to one or more appropriate points in the recuperator heat exchanger that is used in the power production cycle. The choice of temperatures for the injection of heat to the PPS recuperator heat exchanger and the number and inlet temperature of the streams taken from the PPS recuperator heat exchanger to be heated in the quenched fuel gas cooler can be determined by altering the heat recovery process to ensure heat recovery is at the maximum temperature level consistent with economic heat exchanger sizes.

The solid fuel used in the POX reactor can be provided in a variety of forms. In embodiments noted above, a solid fuel can be provided in a particulate form, preferably a finely powdered state, and can be slurried with a slurry medium, such as water, liquid $CO_2$, and combinations thereof. The carbonaceous fuel used in the POX reactor can be a liquid, such as heated bitumen, in which case no slurrying fluid may be needed.

In some embodiments, a POX reactor according to the disclosure can be adapted to operate at a pressure that is higher than the pressure in the power production system combustor. The power production system combustor particularly can use $CO_2$ as the working fluid that is continuously recycled in the system. Preferably, the POX stream can be cooled via heat exchange as described herein, and the cooled POX stream (i.e., a fuel gas) can be used in the power production system without the need for further compression. The POX reactor can comprise any reactor adapted for combustion of a carbonaceous fuel, particularly wherein the fuel is only partially oxidized, and particularly wherein the reactor is adapted to function at a pressure that is greater than the operating pressure of a power production system combustor as described herein. In exemplary, non-limiting embodiments, a POX combustor can utilize transpiration cooling such as described in U.S. Pat. No. 9,416,728 to Palmer et al., U.S. Pat. No. 9,068,743 to Palmer et al., and U.S. Pat. No. 8,986,002 to Palmer et al., the disclosures of which are incorporated herein by reference in their entireties. The POX combustor particularly can be adapted for receiving a fuel stream and an oxygen source for combustion of the fuel stream. Optionally, a catalyst may be included in the POX reactor and/or a catalyst may be introduced to the POX reactor, such as in admixture with the fuel. Optionally, a steam stream may be introduced to the POX reactor.

In further embodiments, a POX reactor according to the disclosure can be adapted to operate at a pressure that is below the pressure of the power production system combustor. In such embodiments, a POX stream for use as a fuel in the power production system combustor can be compressed before passage into the power production system combustor. The POX reactor can comprise any commercially available system. Non-limiting examples of commercially available systems useful according to the present disclosure include a Shell dry powdered coal feed entrained flow reactor, a GE/Texaco quench reactor, a Siemens cooling screen quench reactor, or similar systems. Useful POX reactors can include internal heat transfer sections absorbing radiant heat from the POX burner. In such embodiments, a portion of the high pressure recycled $CO_2$ stream from the power production system can be heated and returned at a higher temperature to the PPS system. For example, recycled $CO_2$ at a temperature of about 400° C. or higher can be heated to a temperature of about 450° C. to about 600° C. within the POX reactor and returned to the recuperative heat exchanger in the power production system where it can be remixed with a further portion of the high pressure recycle $CO_2$ stream at a similar temperature.

Combination of a POX reactor with a power production system according to the present disclosure can provide a variety of useful aspects. As an example, the combination can be defined in that impurities (such as from coal or other solid fuel and from partial oxidation of the fuel) can be retained in the cooled, high pressure POX stream that enters the power production system combustor. Such impurities can comprise $H_2S$, COS, $CS_2$, HCN, $NH_3$, Hg. These and other impurities can be oxidized in the power production system combustor so as to form, for example, $SO_2$, $CO_2$, $N_2$, NO, and Hg, which then can be removed from the power production system. For instance, a water stream condensed from the power production system combustor exit stream can be acidic comprising one or more of $HNO_3$, $H_2SO_4$, and dissolved inorganic salts, such as described in U.S. Patent Application Publication No. 2011/0179799. In one or more embodiments, however, substantially all of the impurities may be removed from the POX fuel stream before being introduced to the PPS combustor. For example, as further described herein, it can be useful to provide the POX stream as an enriched methane stream (i.e., comprising about 20% or greater, about 30% or greater, about 50% or greater, about 60% or greater, about 70% or greater, about 80% or greater, about 90% or greater, or about 95% or greater methane based on the total volume of the POX fuel gas stream introduced to the PPS combustor). The processing of solid fuel through the POX reactor rather than directly through a power production system combustor can be particularly useful in light of the ability to remove possibly fouling reaction products, particularly ash and other solids.

The systems and methods of the present disclosure can be adapted to provide for recovery of substantially all of the heat released during cooling of the POX stream, preferably cooling to near ambient temperature, and recovery of the heat into the recycled high pressure $CO_2$ stream in the power production system. This additional heating particularly can be provided at the lower temperature level in the recuperator heat exchanger of the power production system. Input of additional heat in this manner can provide a significant positive effect on the overall efficiency of the power production system. This effect is due to the much higher specific heat of the high pressure recycle $CO_2$ stream in the lower temperature range of 50° C. to 400° C. compared to the higher temperature range of 400° C. to 800° C. and to the lower specific heat of the turbine exhaust stream that is cooling in the recuperator heat exchanger of the power production system. This marked difference means that significant additional extra heat is required in the recuperator heat exchanger over the temperature range 50° C. to 400° C. to heat the recycle $CO_2$ stream. The additional heat obtained from the quenched POX stream in the POX stream heat exchanger provides an effective quantity of additional heat for the power production system combustor that is substantially equivalent to the quantity of heat released when fuel gas itself is combusted.

In some embodiments, the fuel gas taken from the POX reactor following quench and ash removal can comprise predominantly $H_2$, CO, $CO_2$ and $H_2O$ at a temperature of about 250° C. to about 400° C. A portion of this fuel gas stream can be taken for the production of pure $H_2$, CO, or a combination thereof with varying $H_2$ to CO ratios. Typical applications for large scale $H_2$ production can be, for example, hydro-desulfurization and hydrocracking in refineries and, potentially, as a vehicle fuel. Typical applications for $H_2$ and CO mixtures can be, for example, Fischer-Tropsch hydrocarbon liquids production (e.g., with an $H_2$ to CO ratio of about 1.5 to about 3, particularly about 2.2) and methanol production (e.g., with an $H_2$ to CO ratio of about 1.5 to about 2.5, particularly about 2). In each case, the $H_2$ to CO ratio must be increased from the ratio of approximately 1 or less in the POX fuel gas stream where the ratio depends on the operating parameters of the POX reactor (e.g., temperature and/or pressure), on the use of $CO_2$ or water as the slurrying medium for the solid fuel, and on the $H_2$ to carbon ratio in the solid fuel. Water based slurry with more water in the POX product gas results in a significant proportion of the CO and $H_2O$ being converted to $H_2$ and $CO_2$, giving a $H_2$ to CO ratio of just below 1. $CO_2$ based slurry has a much lower $H_2$ to CO ratio. It can be useful to pass at least part of the separated quenched POX fuel stream through a catalytic shift reactor to convert CO to $H_2$ by reaction with steam, as shown below in Formula (2).

$$CO+H_2O \rightleftharpoons H_2+CO_2 \qquad (2)$$

This can be accomplished using a portion of the fuel gas taken at a temperature of about 250° C. to about 400° C. following ash removal and by using a sulfur tolerant CO shift catalyst, such as one based on cobalt-molybdenum in the shift reactor. The portion of fuel gas that has been enriched in $H_2$ can be then cooled in a separate pass through the POX heat exchanger. Heat released in the exothermic shift reaction can be transferred into the PPS as previously described. The exit shifted gas then can be mixed with a portion of the remaining cooled POX stream and the combined stream can be passed through a multi-bed pressure swing adsorber designed to separate the $H_2$ and CO at the required $H_2$ to CO ratio as a single non adsorbed component while the adsorbed components can contain all of the sulfur compounds, HCN, $NH_3$, Hg, $CO_2$, $H_2O$ and most of the $CH_4$. This un-adsorbed fraction may also contain some $N_2$ and Ar derived from the coal (or other solid or liquid fuel) and oxygen used in the POX reactor. These inert components preferably will be below 5% total concentration which is acceptable for the gas feed to both the Fischer-Tropsch and Methanol reactors. If pure $H_2$ production is required, only the shifted cooled gas will be fed to the PSA. The near atmospheric pressure waste gas from the PSA with all of the coal and POX derived impurities in a reduced form will be compressed and returned to the remaining POX fuel gas for combustion in the PPS combustor.

Figure 1:
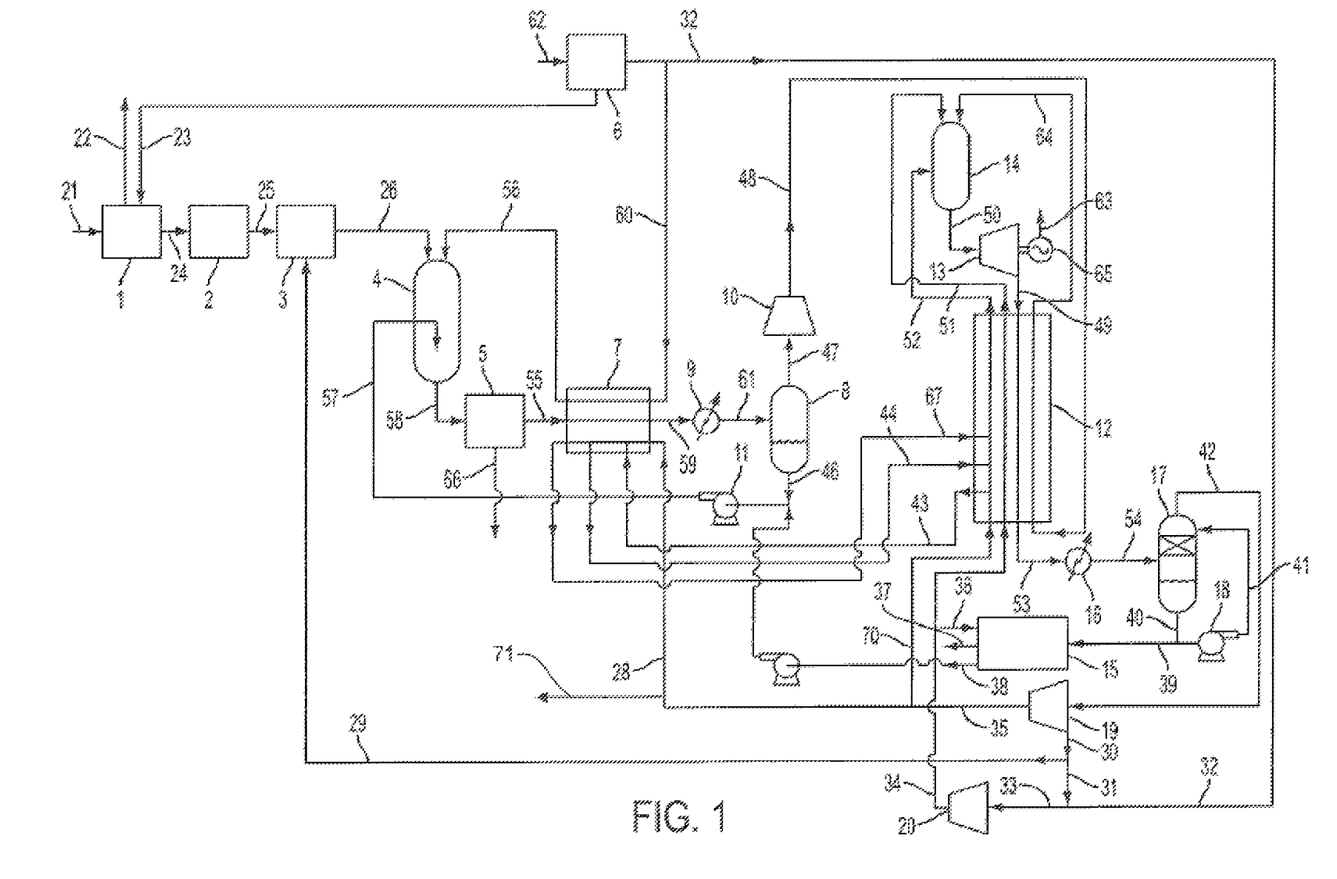
FIG. 1 is flow sheet illustrating an example embodiment of a combined POX system and PPS according to the present disclosure wherein the PPS generates power using a fuel gas derived from the partial oxidation of a liquid or solid hydrocarbon or carbonaceous fuel in the POX system.

One embodiment of a power production system with partial oxidation of a solid fuel is described in reference to FIG. 1, wherein a solid fuel is provided in the form of coal feed stream 21 to be partially oxidized in the POX reactor 4. The coal stream 21 is crushed and partially dried in large particle crusher 1 that is also fed dry nitrogen stream 23 comprising $N_2$ at a temperature of about 82° C. (180° F.) taken from an air separation unit 6, which produces oxygen streams 32 and 60 and nitrogen stream 23 from air intake stream 62. Preferably, the dry nitrogen stream 23 can be heated against a higher temperature stream of $CO_2$ rich turbine exhaust leaving the recuperator heat exchanger in the PPS. The coal is further crushed to a particle size preferably of about 250 microns or less in the small particle crusher 2 to provide particularized coal stream 25, which is directed to a slurry mixer 3. In the slurry mixer 3, the particularized coal is mixed with $CO_2$ slurry medium stream 29, which preferably has a pressure of about 8.5 MPa or greater. The $CO_2$ in the $CO_2$ slurry medium stream 29 in this embodiment is at a temperature of about 17° C. The $CO_2$ in the $CO_2$ slurry medium stream 29 has a density of about 865 kg/m$^3$. The powdered coal is increased in pressure in a lock hopper system or by other means to a pressure of 8.5 MPa prior to mixing with the $CO_2$. A coal/$CO_2$ slurry stream 26 exits the slurry mixer 3 and preferably comprises about 45% by weight coal. Alternatively the slurry medium can be a water stream. The powdered coal injection system can also be configured as a dry feed system in which the powdered pressurized coal is entrained in a nitrogen stream and fed into the POX burner. The slurry stream 26 is then pumped into the POX reactor 4 where it is combined with oxygen stream 56, which preferably comprises 97% molar or greater oxygen concentration. The POX reactor 4 preferably operates at a pressure of about 8.5 MPa and a temperature of about 1400° C.; however, the temperature and pressure can be in any combinations of temperature and pressure ranges as otherwise disclosed herein in relation to the nature of the POX stream exiting the POX reactor. The conditions for the preparation of the coal slurry can be adjusted accordingly.

The POX reactor 4 is adapted to partially oxidize the coal and form a POX stream, which may exit the POX reactor and enter a quench chamber (not illustrated) or may be quenched within the POX reactor itself, as illustrated in FIG. 1. The POX stream can comprise a fuel gas that can comprise one or more combustible (i.e., oxidizable) materials, including but not limited to $H_2$, CO, $CH_4$, $H_2S$, COS, $CS_2$, HCN, $NH_3$. Moreover, the POX stream can comprise Hg and other impurities derived from the coal (or other solid fuel) as well as inert materials (e.g., $N_2$ and Ar), such as derived from the oxygen stream 56, plus other trace components. The POX stream also can comprise one or more non-combustible materials, such as ash or slag, which can be filtered from the POX stream as desired.

The POX stream (either internal to the POX reactor or in a separate component) is quenched by mixing with a quench fluid (liquid water stream 57 in the present embodiment). As illustrated, the liquid water stream 57 enters the POX reactor near the base in a restriction nozzle. The addition of the quench stream cools the POX stream components preferably to below the water saturation temperature of about 304° C. (although higher temperatures also are encompassed). The quench temperature preferably also can be a temperature at which non-combustibles, such as ash and slag, are in solid form. The excess quench water collects with the slag and the bulk of the fine ash in the sump of the POX reactor vessel (or separate quench vessel) where it is removed for further treatment. The quenched POX stream 58 passes to scrubber unit 5, which comprises a water scrub tower followed by a fine cartridge filter adapted to reduce the dust load to about 4 mg/m$^3$ or less of fuel gas, about 3 mg/m$^3$ or less of fuel gas, or about 2 mg/m$^3$ or less of fuel gas. Scrubber unit 5 also can include all equipment and pumps required to recycle the scrub water and also to treat the ash stream 66 for disposal. An exemplary embodiment of a system useful for POX reactor ash treatment and gas cleaning is a GE/Texaco POX system with a coal/water slurry burner, which alternatively can be modified to accept a coal/$CO_2$ slurry.

The cleaned fuel gas plus steam stream 55 is cooled in heat exchanger 7. The exit stream 59 is further cooled against cooling water in heat exchanger 9. Liquid water 46 is separated in separation vessel 8 from the inlet stream 61 and pumped in pump 11 back to the POX reactor quench and some addition makeup water from stream 38 to produce quench water stream 57. The net fuel gas stream 47 is compressed in a multi-stage centrifugal compressor 10 to a pressure suitable for input as stream 48 to the power production system combustor 14. As an example, the fuel gas stream 47 can be compressed to a pressure of about 30.5 MPa. The compressed fuel gas stream 48 is heated in the recuperator heat exchanger 12 to a temperature suitable for input to the power production system combustor 14. As an example, the compressed fuel gas stream 48 can be heated to a temperature of about 746° C. The heated fuel gas stream 64 is burned in the power production system combustor 14 where it is combined with oxygen and $CO_2$. In the illustrated embodiment, combined $O_2/CO_2$ stream 51 comprises 30% $O_2$ and 70% $CO_2$ on a molar basis. The combined $O_2/CO_2$ stream 51 preferably has been heated to a temperature suitable for input to the power production system combustor 14. As an example, the combined $O_2/CO_2$ stream 51 can be heated to a temperature of about 746° C. in the recuperator heat exchanger 12. A hot recycle $CO_2$ stream 52 is directed from the recuperator heat exchanger 12 and is at a temperature suitable for input to the power production system combustor 14. As an example, the hot recycle $CO_2$ stream 52 can be heated to a temperature of about 746° C.

In the power production system combustor, the combustion gases from burning of the fuel gas are cooled with the hot recycle $CO_2$ stream 52 producing a combined combustion product stream 50 at a temperature of about 1150° C. and a pressure of about 30 MPa in the illustrated embodiment. This is expanded to a pressure of about 3 MPa in turbine 13 coupled to an electric generator 65 producing an output power 63. The turbine outlet stream 49 is cooled in the recuperator heat exchanger 12 leaving as cooled product stream 53 at a temperature of about 64° C. in the illustrated embodiment. The stream 53 is cooled to a temperature of about 17° C. in water cooler 16. The further cooled turbine outlet stream 54 enters a scrub tower 17, which has an outlet stream 40 that is largely recycled via circulation pump 18 to scrub tower liquid inlet 41 above the packed section of the tower that receives the further cooled turbine outlet stream 54. A portion of stream 40 is split out as stream 39 for further treatment. As the turbine exhaust gas cools below the water dew-point in the recuperator heat exchanger 12 the following reactions occur.

(3)

(4)

(5)

The above reactions will proceed in the presence of liquid water, nitrogen oxides, $SO_2/SO_3$, and excess oxygen. The $SO_2/SO_3$ concentrations are reduced to very low levels since the limiting reaction shown in Formula (3) rapidly proceeds at 3 MPa, and the reactions of Formula (4) and Formula (5) are very fast. When all of the sulfur oxides have been converted to sulfuric acid, the nitrogen oxides are converted at about 95% conversion rate per pass to nitric acid with the following reaction sequence.

(6)

(7)

(8)

Returning to FIG. 1, the nitric acid present in net liquid acid product stream 39 will convert any mercury present to mercuric-chloride. The scrub tower 17 preferably is fitted with an additional water wash and acid mist removal section. Its primary function is to act as an efficient dilute acid removal device since virtually all the above reactions will have taken place upstream of the scrub tower 17. The mixed acids are treated with limestone slurry stream 36 (or other suitable base) in mixer 15 to produce gypsum and calcium nitrate stream 37. Any other trace metallic salts can also be separated. The residual water stream 38 following calcium nitrate and dissolved salts removal can be used as make-up to a cooling tower or the POX quench system or as scrub water recycled to scrub tower 17.

The predominantly $CO_2$ stream 42 leaving the scrub tower 17 at a pressure of about 2.9 MPa is compressed in a multi-stage intercooled compressor 19 followed by a dense fluid multistage pump to a pressure suitable for input to the power production system combustor, such as about 30.5 MPa. The compressed $CO_2$ discharge stream 35 leaves the last stage of the pump 19 at a temperature of about 54° C., and part of this flow, stream 70, is heated in the recuperator heat exchanger 12 to a temperature of about 746° C., leaving as $CO_2$ stream 52.

The air separation plant 6 in this embodiment produces a 99.5% molar oxygen purity product stream at a pressure of about 8.6 MPa which divides into two separate streams. Oxygen stream 60 is heated in heat exchanger 7 to a temperature of about 294° C., exiting as stream 56 for use in the POX reactor 4 for partial oxidation of the coal. The remaining oxygen stream 32 is mixed with $CO_2$ at a pressure of about 8.6 MPa. Specifically, $CO_2$ is taken from an intermediate stage of the compressor 19 as stream 30, and a portion stream 31 mixes with oxygen stream 32 giving a composition of about 30% $O_2$ and 70% $CO_2$ molar. This diluted $O_2$ stream 33 is compressed to a pressure of about 30.5 MPa in a multi-stage intercooled compressor 20 and the discharge stream 34 is heated in the recuperator heat exchanger 12 to a temperature of about 746° C. and enters the power production system combustor 14 as stream 51. Dilution of the pure $O_2$ stream 32 is beneficial to allow the oxygen required for combustion in the power production system combustor 14 to be heated to a high temperature without the need for oxidation resistant materials. This ensures the safe operation of the power production system. The 30% $O_2$ stream is useful to moderate the adiabatic combustion temperature in power production system 14 to a value of approximately 2400° C. The remaining portion of $CO_2$ stream 30 is $CO_2$ stream 29, which provides the $CO_2$ for slurrying the powdered coal and is directed to slurry mixer 3.

Cooling of the quenched POX gas in heat exchanger 7 is useful to transfer the maximum quantity of heat to the power production system to maximize the overall efficiency. The power production system requires a significant quantity of heat from an external source in the temperature range from near ambient up to about 400° C. This can be provided by using adiabatic air compressors in the air separation plant 6 and transferring the heat of compression to part of the high pressure recycle $CO_2$ stream. In the present embodiment, the required external heating load is provided by cooling the quenched POX gas in heat exchanger 7 and heating two high pressure recycle streams. High pressure recycle $CO_2$ stream 28 at a temperature of about 54° C. and high pressure recycle $CO_2$ stream 43 at a temperature of about 120° C. taken from an intermediate temperature point in recuperator heat exchanger 12 are heated to provide a combined heating outlet stream 44 at a temperature of about 294° C., which is returned to mix with the main recycle $CO_2$ stream at a corresponding temperature point in recuperator heat exchanger 12. Optionally, outlet stream 67 also may be returned to the recuperator heat exchanger at a corresponding temperature point to mix with the main recycle $CO_2$ stream as well.

In exemplary embodiments, heat exchanger 7 can be a high pressure brazed or diffusion bonded multi-channel unit. The material of construction preferably is corrosion resistant in the presence of the impurities present in the POX gas plus liquid water. Recuperator heat exchanger 12 preferably is a diffusion bonded multi-channel unit. This unit preferably is adapted for operation at temperatures up to about 800° C. and to be resistant to acid corrosion at temperatures above about 200° C. An exemplary suitable material is Specialty Metals alloy 740. In some embodiments, the average temperature at the hot end of heat exchanger 12 can be reduced to below 750° C. and, in such cases, alloy 617 can be suitable. Optionally the intermediate section between 200° C. and 540° C. can be fabricated from stainless steel. The section which is subject to potential acid corrosion below 200° C. can be constructed to allow replacement at intervals.

In one or more embodiments, the POX system can be configured to provide a fuel stream that is enriched in methane. Such POX system can incorporate any of the elements otherwise described herein. In particular, such POX system can comprise a catalytic POX reactor that can be configured to partially oxidize a solid or liquid fuel with oxygen in the presence of a catalyst and optionally steam to form a POX product stream that is enriched in methane content as compared to partial oxidation in the absence of the catalyst. The catalyst can comprise any catalyst suitable for promoting methane production in partial oxidation of a carbonaceous or hydrocarbon fuel. For example, suitable catalysts can include alkali metals, alkaline earth metals, transition metals, compounds thereof, complexes thereof, and combinations thereof. Nickel or supported nickel catalysts, for example, can be useful. Examples of catalytic POX reaction components that may be utilized according to embodiments of the present disclosure to produce a POX fuel stream with a relatively high methane content are described in U.S. Pat. Pub. Nos. 2003/0167961, 2006/0265953, 2007/000177, 2007/083072, 2007/0277437, 2009/0048476, 2009/0090056, 2009/0090055, 2009/0165383, 2009/0166588, 2009/0165379, 2009/0170968, 2009/0165380, 2009/0165381, 2009/0165361, 2009/0165382, 2009/0169449, 2009/0169448, 2009/0165376, 2009/0165384, 2010/0076235, 2011/0031439, 2011/0062721, and 2011/0064648, the disclosures of which are incorporated herein by reference.

In some embodiments, a POX system configured for increased methane content can be specifically operated under relatively mild conditions. For example, the POX reactor may be operated at a temperature of about 1000° C. or less, about 800° C. or less, about 600° C. or less, or about 400° C. or less (e.g., with a lower limit of about 200° C.). More particularly, the POX reactor may be operated at a temperature of about 300° C. to about 1000° C., about 325° C. to about 900° C., about 350° C. to about 800° C., or about 400° C. to about 700° C.

An example embodiment of a POX system with methanation is described below in relation to FIG. 2. As seen therein, a solid fuel stream 115, an oxygen source stream 56, and a steam stream 116 are injected into the POX reactor 4 for partial oxidation of the solid fuel. A catalyst can also be provided to the POX reactor 4. The catalyst may be stationary in the POX reactor and/or may be fluid. For example, particularized catalyst may be combined with the fuel stream 115. The steam stream 116 input to the POX reactor 4 can be beneficial to provide for control of the operating temperature with a desired range and/or to maximize the methane yield in the product stream. A POX product stream 85 exiting the POX reactor 4 can comprise any combination of $H_2$, CO, $CO_2$, $H_2O$, char, $CH_4$, $H_2S$, COS, $CS_2$, HCN, and $NH_3$. In one or more embodiments, the utilization of the catalytic reaction can be beneficial to significantly increase the methane content of the POX combustion stream beyond that which would otherwise be possible. Thus, the POX product stream 85 exiting the POX reactor 4 can be characterized as being enriched in methane content. A methane-enriched stream can comprise at least 5%, at least 10%, at least 20%, or at least 30% by volume (e.g., 5% to 95%, 10% to 75%, or 20% to 60%) more methane than is present in the corresponding stream formed without the use of the catalyst. In some embodiments, the POX product stream 85 exiting the POX reactor 4 can have a methane content of at least 10%, at least 15%, at least 20%, or at least 25% by volume (with an upper maximum methane content of 95%, 85%, or 75% by volume) based on the total volume of the POX product stream.

The POX product stream 85 is passed to a convective cooler 86 to cool the POX combustion stream to about 500° C. or less, about 400° C. or less, or about 300° C. or less (with a lower limit of about 100° C.). The cooling stream used in the convective cooler 86 can comprise a high pressure recycle fluid stream withdrawn from and returned to the PPS, a high pressure stream of water, a nitrogen stream withdrawn from an air separation unit for the solid fuel drying process, a high pressure $O_2/CO_2$ stream, and/or a cleaned and cooled POX fuel gas stream. Other cooling units can be used in addition or in the alternative, including but not limited a quenching unit.

The cooled POX product stream 87 exiting the convective cooler 86 is directed to a filter unit 88 to remove solids from the POX product stream. The solids stream 117 drawn from the filter unit 88 can include, for example, ash particles, unburned char, and catalyst. Any catalyst taken from solids stream 117 can be sent to a catalyst recovery system for catalyst recycling, such as described in U.S. Pat. Pub. No. 2010/0168495 and U.S. Pat. Pub. No. 2011/0031439, the disclosures of which are incorporated herein by reference.

The cooled and filtered POX product stream 89 exiting the filter unit 88 passes to a water scrubber unit 90 that can be configured to remove all fine particles. Additionally, the water scrubber unit 90 can be configured to remove any soluble acid gas, such as $NH_3$.

The cleaned POX fuel stream 91 can undergo one or more conversion steps to alter the composition of the stream. As illustrated in FIG. 2, the cleaned POX fuel stream 91 is passed through a splitter 92 to split the stream in a first fraction stream 93 and a second fraction stream 94. The POX fuel first fraction stream 93 is sent to a catalytic COS hydrolysis unit 95 for converting COS to $H_2S$. The POX fuel second fraction stream 94 is directed to a catalytic water gas shift reactor 96 to convert CO and $H_2O$ to $CO_2$ and $H_2$. The streams exiting the catalytic COS hydrolysis unit 95 and the catalytic water gas shift reactor 97 can be combined as POX fuel stream 97. If desired, the entire POX fuel stream 91 can be processed through the catalytic COS hydrolysis unit 95, or the entire POX fuel stream 91 can be process through the catalytic water gas shift reactor 96. For example, in one or more embodiments, the catalyst used in the water gas shift reactor 96 can be configured to also hydrolyze COS. Thus, the catalytic COS hydrolysis unit 95 may be absent. The split ratio of the splitter 92 can be determined by fixing the $H_2$/CO ratio of the POX fuel stream 97. For example, the $H_2$/CO ratio of the POX fuel stream 97 can be about 5:1 to about 1:1, about 4:1 to about 2:1, or approximately 3:1. The ratio may be defined based upon the desired final methane content in light of the downstream methanation process that will be carried out wherein $CO+3H_2$ yields $CH_4+H_2O$. For example, a 3:1 ratio can be particularly useful for achieving a final syngas with a methane content of greater than 90% by volume.

The POX fuel stream 97 is passed through the POX heat exchanger 7 to withdraw a quantity of heat by cooling the POX fuel stream to a temperature of about 100° C. or less against a cooling stream. For example, as illustrated, oxygen stream 60 is heated in the POX heat exchanger 7 against the POX fuel stream 97 and exits as stream 56 (which can be used in the POX reactor 4 for partial oxidation of the coal—as shown in FIG. 1). The high pressure recycle $CO_2$ stream 28 and the high pressure recycle $CO_2$ stream 43 (previously discussed in relation to FIG. 1) can be heated in the POX heat exchanger to provide a combined heating outlet stream 44 that is mixed with the main recycle $CO_2$ stream in recuperator heat exchanger 12. Outlet stream 67 also may be returned to the recuperator heat exchanger 12 to mix with the main recycle $CO_2$ stream.

POX fuel stream 98 exiting the POX heat exchanger 7 can be further cooled with cooling water in heat exchanger 99, such as to a temperature of about 35° C. The POX fuel stream 100 exiting the water cooling heat exchanger 99 is passed through separator 101 from which condensed water stream 103 can be withdrawn. Depending upon the composition of the POX fuel gas (which can vary based upon the composition of the fuel that is oxidized in the POX reactor), further cleaning of the POX fuel gas can be desirable. As illustrated in the embodiment of FIG. 2, the POX fuel stream 102 is passed to a mercury and acid gas removal unit 104. Exemplary acid gas streams exiting the unit 104 can include an $H_2S$ stream 105 and a $CO_2$ stream 106 (although other acid gases also may be withdrawn). The $H_2S$ stream 105 can be converted into liquid elemental sulfur, such as using the Claus process, as one example, or can be converted into a commercial quality sulfuric acid, such as using the wet sulfuric acid process, for example. The $CO_2$ stream 106 removed from the acid gas removal unit can be compressed and merged into the compressed recycle $CO_2$ stream 35 in FIG. 1 or may be used otherwise or sequestered. In various embodiments, a separate mercury removal unit may be used, a separate acid gas removal may be used, or a combined mercury and acid gas removal unit may be used.

A non-limiting example of a mercury removal unit can include an activated, sulfur-impregnated, carbon bed adsorption system. As non-limiting examples, acid gas removal can proceed with the use of one or any combination of chemical reagents, physical solvents, and hybrid solvents. Specific, non-limiting examples of acid gas removal process that may be utilized include: methanol solvent systems (e.g., REC-TISOL®); composite solvent systems (e.g., SULFINOL®, which is a mixture of diisopropanolamine (30-45%) or methyl diethanolamine (MDEA), sulfolane (tetrahydrothiophene dioxide) (40-60%), and water (5-15%)); amine treatment systems (e.g., utilizing diethanolamine (DEA), monoethanolamine (MEA), methyl diethanolamine (MDEA), and diisopropanolamine (DIPA)); SELEXOL™ i.e., (dimethyl ethers of polyethylene glycol); and FLEXSORB™ (i.e., sterically hindered amines). One exemplary method can include the use of a two stage SELEXOL™ process (available from UOP LLC, USA), wherein $H_2S$ is removed at the first stage, and $CO_2$ is removed at the second stage.

The POX fuel stream 107 can be passed into a methanation unit 108 that can be configured to convert CO and $H_2$ to $CH_4$ and $H_2O$. The methanation unit 108 can be a catalytic unit utilizing, for example, a nickel-based catalyst. A non-limiting example of a methanation process that can be carried out in the methanation unit 108 is the high temperature TREMP™ Process described in U.S. Pat. No. 8,530,529, the disclosure of which is incorporated herein by reference.

The POX fuel stream 109 exiting the methanation unit 108 can be characterized as being a methane-enriched POX fuel gas and can have a methane content of about 50% or greater, about 60% or greater, about 70% or greater, about 80% or greater, about 85% or greater, about 90% or greater, or about 95% or greater methane by volume (with an upper limit of 99.9%) based upon the total volume of the stream. Heat released from the methanation process can be recuperated in one or more heat exchangers that can be integrated with the methanation unit 108 or be utilized as added components.

The methane-enriched POX fuel stream 109 can be further cooled in a water cooled heat exchanger 110, such as to a temperature of about 20° C. The cooled, methane-enriched POX fuel stream 111 can be passed through a separator 112 to remove water in stream 114, the water having been produced in the methanation unit 108.

The cooled, clean, methane-enriched POX fuel gas stream 113 can be compressed utilizing a compressor as shown in FIG. 1. For example, the POX fuel gas stream 113 can be compressed to a pressure of about 30.5 MPa in compressor 10 in FIG. 1, and the compressed POX fuel gas can then be sent to the power production system. The condensed water streams 103 and 114 can be pumped to a pressure which is slightly higher than the operating pressure of the POX reactor 4, and the pressurized streams can be heated in the convective cooler 86, and/or in the POX heat exchanger 7, and/or in the PPS heat exchanger 12 (see FIG. 1) to form steam, at least a portion of which can be used in stream 116 input to the POX reactor 4.

Figure 2:
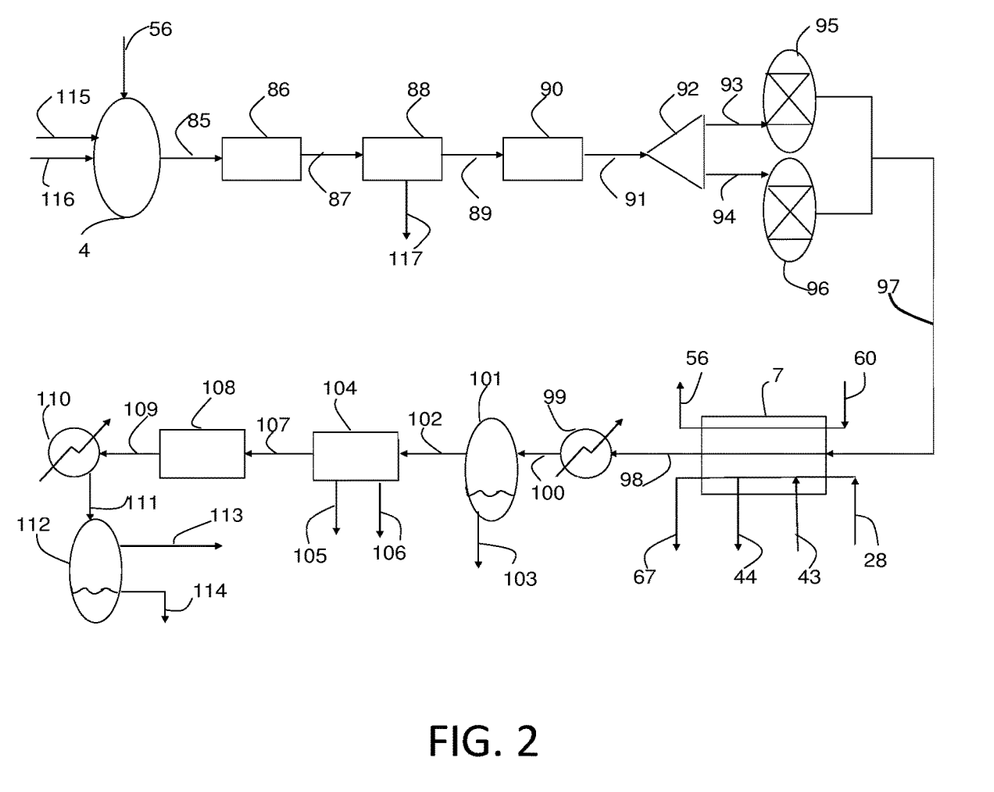
FIG. 2 is a flow sheet illustrating an example embodiment of a POX system that can be combined with a PPS, wherein the POX system is configured to provide a methane-enriched fuel stream.

In one or more embodiments, certain components of the POX system illustrated in relation to FIG. 2 can be absent. For example, referring to FIG. 2, the cleaned POX fuel stream 91 exiting the water scrubber unit 90 can be passed directly to the POX heat exchanger 7. The POX fuel gas stream 98 still can be further cooled by the cooling water in heat exchanger 99 (e.g., to a temperature of about 20° C.), and condensed water can be separated in separator 101 and withdrawn as condensed water stream 103. The cooled POX fuel stream 102 substantially free of liquid water can be passed directly to the compressor 10 in FIG. 1 where it can be compressed, for example, to a pressure of about 30.5 MPa, and then sent to the power production system in FIG. 1. A simplified system as described in relation to FIG. 2 can be beneficial, for example, to reduce capital costs and operating costs. Moreover, overall system efficiency can be increased in light of reduced parasitic loads to the system.

Many modifications and other embodiments of the presently disclosed subject matter will come to mind to one skilled in the art to which this subject matter pertains having the benefit of the teachings presented in the foregoing descriptions and the associated drawings. Therefore, it is to be understood that the present disclosure is not to be limited to the specific embodiments described herein and that modifications and other embodiments are intended to be included within the scope of the appended claims. Although specific terms are employed herein, they are used in a generic and descriptive sense only and not for purposes of limitation.

The invention claimed is:

1. A process for the production of power using a combination of a partial oxidation (PDX) system and a power production system (PPS), the process comprising:
   combining a solid or liquid fuel, oxygen, and a catalyst in a PDX reactor under conditions sufficient to partially oxidize the fuel and form a PDX product stream comprising methane;
   cooling the PDX product stream to a temperature of about 500° C. or less;
   separating one or more of solids, molten metals, and acid gases from the cooled PDX product stream to produce a cooled and filtered PDX product stream;
   passing the cooled and filtered PDX product stream through a splitter to split the cooled and filtered PDX product stream in a first fraction stream and a second fraction stream, the first fraction stream being passed through a catalytic water gas shift reactor configured to convert CO and $H_2O$ in the cooled and filtered PDX product stream to $CO_2$ and $H_2$, and the second fraction stream being passed through a carbonyl sulfide (COS) hydrolysis reactor configured to convert COS to $H_2S$, wherein the first fraction stream exiting the catalytic water gas shift reactor and the second product stream exiting the COS hydrolysis reactor combine to form a PDX fuel stream;
   passing the PDX fuel stream to a PDX heat exchanger and withdrawing a quantity of heat from the PDX fuel stream by cooling the PDX fuel stream to a temperature of about 100° C. or less against a cooling stream and form a PDX fuel gas stream comprising methane;
   passing the PDX fuel gas stream through a separator vessel and separating at least a portion of any water present in the PDX fuel gas stream;
   compressing the filtered PDX fuel gas stream to a pressure of about 12 MPa or greater;
   combusting the filtered and compressed PDX fuel gas in a PPS combustor to form a combustion product stream at a pressure of at least about 10 MPa and a temperature of at least about 800° C.; and
   expanding the combustion product stream across a PPS turbine to generate power and form an expanded PPS combustion product stream;
   wherein the filtered PDX fuel gas stream that is compressed to a pressure of about 12 MPa or greater has a methane content of about 20% or greater by volume based on the total volume of the filtered PDX fuel gas stream.

2. The process of claim 1, wherein the catalyst used in the PDX reactor is selected from the group consisting of alkali metals, alkaline earth metals, transition metals, compounds thereof, complexes thereof, and combinations thereof.

3. The process of claim 1, wherein the PDX reactor is operated at a temperature of about 1000° C. or less.

4. The process of claim 1, further comprising adding steam to the PDX reactor.

5. The process of claim 1, wherein cooling the PDX product stream from the PDX reactor comprises passing the PDX product stream through a convective cooler against a cooling stream.

6. The process of claim 5, wherein the cooling stream comprises one or more of:
   a high pressure recycle fluid stream withdrawn from and returned to the PPS;
   a high pressure water stream;
   a nitrogen stream;
   a stream of PDX reactor liquid fuel feed;
   a high pressure stream of $O_2$ and $CO_2$; and
   a stream of cleaned and cooled PDX fuel gas.

7. The process of claim 1, wherein the solids separated from the cooled PDX product stream comprise one or more of ash particles, unreacted char, and catalyst.

8. The process of claim 1, wherein the separating of the one more of solids, molten metals, and acid gases from the cooled PDX product stream comprises passing the cooled PDX product stream through a particle filter and a water scrubber.

9. The process of claim 1, wherein the first fraction stream exiting the catalytic water gas shift reactor has an $H_2$ to CO ratio of about 5:1 to about 1:1.

10. The process of claim 1, wherein the PDX fuel stream passed through the PDX heat exchanger is cooled against a cooling stream comprising one or more of:
    a high pressure recycle fluid stream withdrawn from and returned to the PPS;
    a high pressure water stream;
    a nitrogen stream;
    a stream of PDX reactor liquid fuel feed;
    a high pressure stream of $O_2$ and $CO_2$; and
    a stream of cleaned and cooled PDX fuel gas.

11. The process of claim 1, wherein prior to compressing the filtered PDX fuel gas stream to a pressure of about 12 MPa or greater, at least a portion of the filtered PDX fuel gas stream is passed through one or both of a mercury removal unit and an acid gas removal unit.

12. The process of claim 11, wherein at least a portion of the filtered PDX fuel gas stream is passed through an activated, sulfur-impregnated, carbon bed adsorption system configured to remove mercury from the PDX fuel gas.

13. The process of claim 11, wherein at least a portion of the filtered PDX fuel gas stream is passed through an acid gas removal unit configured to remove part or substantially all of at least one of $H_2S$ and $CO_2$ from the filtered PDX fuel gas stream.

14. The process of claim 1, wherein prior to the step of compressing the filtered PDX fuel gas stream to a pressure of about 12 MPa or greater, at least a portion of the filtered PDX fuel gas stream is passed through a methanation unit configured to convert CO and $H_2$ to $CH_4$ and $H_2O$.

15. The process of claim 14, wherein the methanation unit is a catalytic unit, and optionally wherein methanation is carried out using a nickel-based catalyst.

16. The process of claim 14, wherein the methane-enriched PDX fuel gas exiting the methanation unit has a methane content of about 50% or greater by volume.

17. The process of claim 14, comprising passing the methane-enriched PDX fuel gas exiting the methanation unit through a post-methanation heat exchanger against a cooling stream, optionally wherein the cooling stream comprises one or more of: a high pressure recycle fluid stream withdrawn from and returned to the PPS; a high pressure water stream;

a nitrogen stream; a high pressure stream of $O_2$ and $CO_2$; a stream of PDX reactor liquid fuel feed; and a stream of cleaned and cooled PDX fuel gas.

18. The process of claim 14, comprising passing the methane-enriched PDX fuel gas stream from the methanation unit to a separator wherein at least a portion of any water produced in the methanation reactor is removed.

19. The process of claim 1, wherein after compressing the filtered PDX fuel gas stream to a pressure of about 12 MPa or greater and prior to combusting the filtered and compressed PDX fuel gas in the PPS combustor, the process comprises heating the filtered and compressed PDX fuel gas by passage through the PDX heat exchanger.

20. The process of claim 1, further comprising:
passing the expanded PPS combustion product stream through a PPS recuperator heat exchanger and thereby withdrawing heat from the PPS combustion product stream and forming a cooled PPS combustion product stream;
optionally passing the cooled PPS combustion product stream through a water cooler;
treating the cooled PPS combustion product stream in a PPS scrubber to form a recycle $CO_2$ stream by removing substantially all non$CO_2$ components; and
pressurizing the recycle $CO_2$ stream in a PPS compressor to form a compressed recycle $CO_2$ stream.

* * * * *